United States Patent
May et al.

(10) Patent No.: US 11,103,311 B2
(45) Date of Patent: Aug. 31, 2021

(54) AUGMENTED REALITY SUPPORTED KNEE SURGERY

(71) Applicant: Biomet Manufacturing, LLC, Warsaw, IN (US)

(72) Inventors: Brian M. May, Orange, CT (US); William Hartman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 507 days.

(21) Appl. No.: 15/907,897

(22) Filed: Feb. 28, 2018

(65) Prior Publication Data

US 2018/0256256 A1 Sep. 13, 2018

Related U.S. Application Data

(60) Provisional application No. 62/469,815, filed on Mar. 10, 2017.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/20* (2016.02); *A61B 34/25* (2016.02); *A61B 90/36* (2016.02);
(Continued)

(58) Field of Classification Search
CPC ......... A61B 34/10; A61B 34/25; A61B 90/36; A61B 34/20; A61B 6/461; A61B 5/742; A61B 2034/2055; A61B 2090/365; A61B 2034/105; A61B 2034/108; G06T 19/006; G06T 19/003; G06T 2210/41; A61F 2/461; A61F 2002/4633
See application file for complete search history.

(56) References Cited

U.S. PATENT DOCUMENTS 6,856,324 B2 2/2005 Sauer et al.
7,176,936 B2 2/2007 Sauer et al.
(Continued)

FOREIGN PATENT DOCUMENTS

CN 102341046 A 2/2012
CN 110603002 12/2019
(Continued)

OTHER PUBLICATIONS

"Australian Application Serial No. 2018230901, First Examination Report dated Dec. 20, 2019", 5 pages.
(Continued)

*Primary Examiner* — Sanjay Cattungal
(74) *Attorney, Agent, or Firm* — Schwegman Lundberg & Woessner, P.A.

(57) ABSTRACT

Systems and methods may use an augmented reality device during a surgical procedure. The systems and methods may use an augmented reality display of an augmented reality device to present or project a virtual feature during a surgical procedure while permitting physical aspects of a surgical field to be viewed through the augmented reality display. The virtual feature may include aspects of a preoperative plan, a surgical device, an anatomical aspect of a patient, etc.

17 Claims, 9 Drawing Sheets

(51) Int. Cl.
*G06T 19/00* (2011.01)
*A61B 90/00* (2016.01)
*A61F 2/46* (2006.01)
*A61B 34/20* (2016.01)
*A61B 6/00* (2006.01)
*A61B 5/00* (2006.01)

(52) U.S. Cl.
CPC ............ *A61F 2/461* (2013.01); *G06T 19/003* (2013.01); *G06T 19/006* (2013.01); *A61B 5/742* (2013.01); *A61B 6/461* (2013.01); *A61B 2034/105* (2016.02); *A61B 2034/108* (2016.02); *A61B 2034/2055* (2016.02); *A61B 2090/365* (2016.02); *A61F 2002/4633* (2013.01); *G06T 2210/41* (2013.01)

(56) References Cited

U.S. PATENT DOCUMENTS

| | | | |
|---|---|---|---|
| 7,605,826 B2 | 10/2009 | Sauer | |
| 7,774,044 B2 | 8/2010 | Sauer et al. | |
| 7,896,869 B2 | 3/2011 | Disilvestro et al. | |
| 8,010,180 B2 | 8/2011 | Quaid et al. | |
| 8,314,815 B2 | 11/2012 | Navab et al. | |
| 8,509,503 B2 | 8/2013 | Nahum et al. | |
| 8,860,760 B2 | 10/2014 | Chen et al. | |
| 9,002,426 B2 | 4/2015 | Quaid et al. | |
| 9,037,297 B2 | 5/2015 | Hosek | |
| 9,220,572 B2 | 12/2015 | Meridew et al. | |
| 9,360,934 B2 | 6/2016 | Ruiz Morales et al. | |
| 9,439,736 B2 | 9/2016 | Olson | |
| 9,498,132 B2 | 11/2016 | Maier-Hein et al. | |
| 9,538,962 B1 | 1/2017 | Hannaford et al. | |
| 9,560,318 B2 | 1/2017 | Reina et al. | |
| 9,582,079 B2 | 2/2017 | Bock-Krausen et al. | |
| 9,643,314 B2 | 5/2017 | Guerin et al. | |
| 9,652,591 B2 | 5/2017 | Moctezuma De La Barrera et al. | |
| 9,665,960 B1 | 5/2017 | Masters et al. | |
| 9,681,925 B2 | 6/2017 | Azar et al. | |
| 9,737,326 B2 | 8/2017 | Worrell et al. | |
| 9,767,608 B2 | 9/2017 | Lee et al. | |
| 9,775,681 B2 | 10/2017 | Quaid et al. | |
| 9,852,546 B2 | 12/2017 | Kraver et al. | |
| 9,861,446 B2* | 1/2018 | Lang ................... | A61F 2/3859 |
| 9,892,564 B1 | 2/2018 | Cvetko et al. | |
| 9,910,497 B2 | 3/2018 | Kramer et al. | |
| 9,980,780 B2 | 5/2018 | Lang | |
| 10,008,017 B2 | 6/2018 | Itkowitz et al. | |
| 10,010,379 B1 | 7/2018 | Gibby et al. | |
| 10,013,808 B2 | 7/2018 | Jones et al. | |
| 10,105,187 B2 | 10/2018 | Corndorf et al. | |
| 10,159,530 B2 | 12/2018 | Lang | |
| 10,194,131 B2 | 1/2019 | Casas | |
| 10,194,990 B2 | 2/2019 | Amanatullah et al. | |
| 10,231,786 B2 | 3/2019 | Ferro et al. | |
| 10,231,790 B2 | 3/2019 | Quaid et al. | |
| 10,278,777 B1 | 5/2019 | Lang | |
| 10,285,765 B2 | 5/2019 | Sachs et al. | |
| 10,292,768 B2 | 5/2019 | Lang | |
| 10,326,975 B2 | 6/2019 | Casas | |
| 10,357,322 B2 | 7/2019 | Olson | |
| 10,368,947 B2 | 8/2019 | Lang | |
| 10,390,891 B2 | 8/2019 | Govari et al. | |
| 10,405,927 B1 | 9/2019 | Lang | |
| 10,475,244 B2 | 11/2019 | Cvetko et al. | |
| 10,548,667 B2 | 2/2020 | Flett et al. | |
| 10,594,998 B1 | 3/2020 | Casas | |
| 10,595,844 B2 | 3/2020 | Nawana et al. | |
| 10,602,114 B2 | 3/2020 | Casas | |
| 10,603,113 B2 | 3/2020 | Lang | |
| 10,646,283 B2 | 5/2020 | Johnson et al. | |
| 10,646,285 B2 | 5/2020 | Siemionow et al. | |
| 10,650,594 B2 | 5/2020 | Jones et al. | |
| 10,742,949 B2 | 8/2020 | Casas | |
| 10,743,939 B1 | 8/2020 | Lang | |
| 10,786,327 B2 | 9/2020 | Anderson et al. | |
| 10,788,672 B2 | 9/2020 | Yadav et al. | |
| 10,803,608 B1 | 10/2020 | Na et al. | |
| 2006/0281971 A1* | 12/2006 | Sauer ..................... | A61B 34/20 600/109 |
| 2012/0157887 A1* | 6/2012 | Fanson .................. | A61B 90/39 600/595 |
| 2014/0275760 A1* | 9/2014 | Lee ........................ | A61B 34/30 600/102 |
| 2016/0191887 A1* | 6/2016 | Casas ................... | H04N 13/156 348/47 |
| 2016/0228193 A1 | 8/2016 | Moctezuma de la Barrera et al. | |
| 2016/0287337 A1* | 10/2016 | Aram ..................... | A61B 90/37 |
| 2017/0071673 A1* | 3/2017 | Ferro ................... | A61B 5/0077 |
| 2017/0312031 A1* | 11/2017 | Amanatullah ......... | G09B 23/30 |
| 2017/0312032 A1* | 11/2017 | Amanatullah ......... | G09B 23/30 |
| 2018/0078316 A1* | 3/2018 | Schaewe .............. | A61B 5/7435 |
| 2018/0082480 A1* | 3/2018 | White .................... | A61B 50/33 |
| 2018/0092699 A1* | 4/2018 | Finley ................. | A61B 17/7062 |
| 2019/0142520 A1 | 5/2019 | Vandyken | |
| 2019/0231432 A1* | 8/2019 | Amanatullah ........ | G06T 19/006 |
| 2019/0231433 A1* | 8/2019 | Amanatullah ..... | A61B 17/1703 |

FOREIGN PATENT DOCUMENTS

| | | |
|---|---|---|
| DE | 102006056399 A1 | 5/2007 |
| EP | 3654867 A1 | 5/2020 |
| WO | 2017015738 | 2/2017 |
| WO | 2018052966 | 3/2018 |
| WO | 2018078723 | 5/2018 |
| WO | WO-2018164909 A1 | 9/2018 |

OTHER PUBLICATIONS

"Australian Application Serial No. 2018230901, Response filed Jan. 29, 2020 to First Examination Report dated Dec. 20, 2019", 16 pages.
"Australian Application Serial No. 2018230901, Subsequent Examiners Report dated Jan. 30, 2020", 4 pages.
"International Application Serial No. PCT US2018 020201, International Search Report dated Jun. 26, 2018", 7 pgs.
"International Application Serial No. PCT US2018 020201, Written Opinion dated Jun. 26, 2018", 9 pgs.
Smith, N.L., et al., "Development of an Augmented Reality-Guided Computer-Assisted Orthopaedic Surgery System", University of Strathclyde—Published Online:Feb. 21, 2018, [Online]. [Accessed Jul. 26, 2018]. Retrieved from the Internet: URL: http://www.bjjprocs.boneandjoint.org.uk/content/98-B/SUPP_16/18>, (2018), 2 pgs.
"Australian Application Serial No. 2018230901, Response filed Nov. 27, 2020 to Subsequent Examiners Report dated Jan. 30, 2020", 17 pgs.
"European Application Serial No. 18713430.9, Response to Communication pursuant to Rules 161(1) and 162 EPC filed Jun. 2, 2020", 17 pages.
"Canadian Application Serial No. 3,055,244, Office Action dated Jan. 22, 21", 3 pgs.

* cited by examiner

AUGMENTED REALITY SUPPORTED KNEE SURGERY

CLAIM OF PRIORITY

This application claims the benefit of priority to U.S. Provisional Application Ser. No. 62/469,815, filed Mar. 10, 2017, titled "Augmented Reality Supported Knee Surgery" which is hereby incorporated herein by reference in its entirety.

BACKGROUND

Total knee arthroplasty surgeries are performed over half a million times a year in the United States. Surgical advancements have allowed surgeons to use preoperative planning, display devices within a surgical field, optical imaging, and guides to improve surgical outcomes and customize surgery for a patient. While these advances have allowed for quicker and more successful surgeries in some cases, they ultimately rely on physical objects, which have costs and time requirements for manufacturing and configuration. Physical objects and devices may also obstruct portions of a surgical field, detracting from their benefits. Additionally, many of these technological advances end up taking additional surgical time or significantly increase the cost of the procedure. Further, some of these technological advances remove the ability of the surgeon to use his/her experience to make critical decisions during the surgical procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
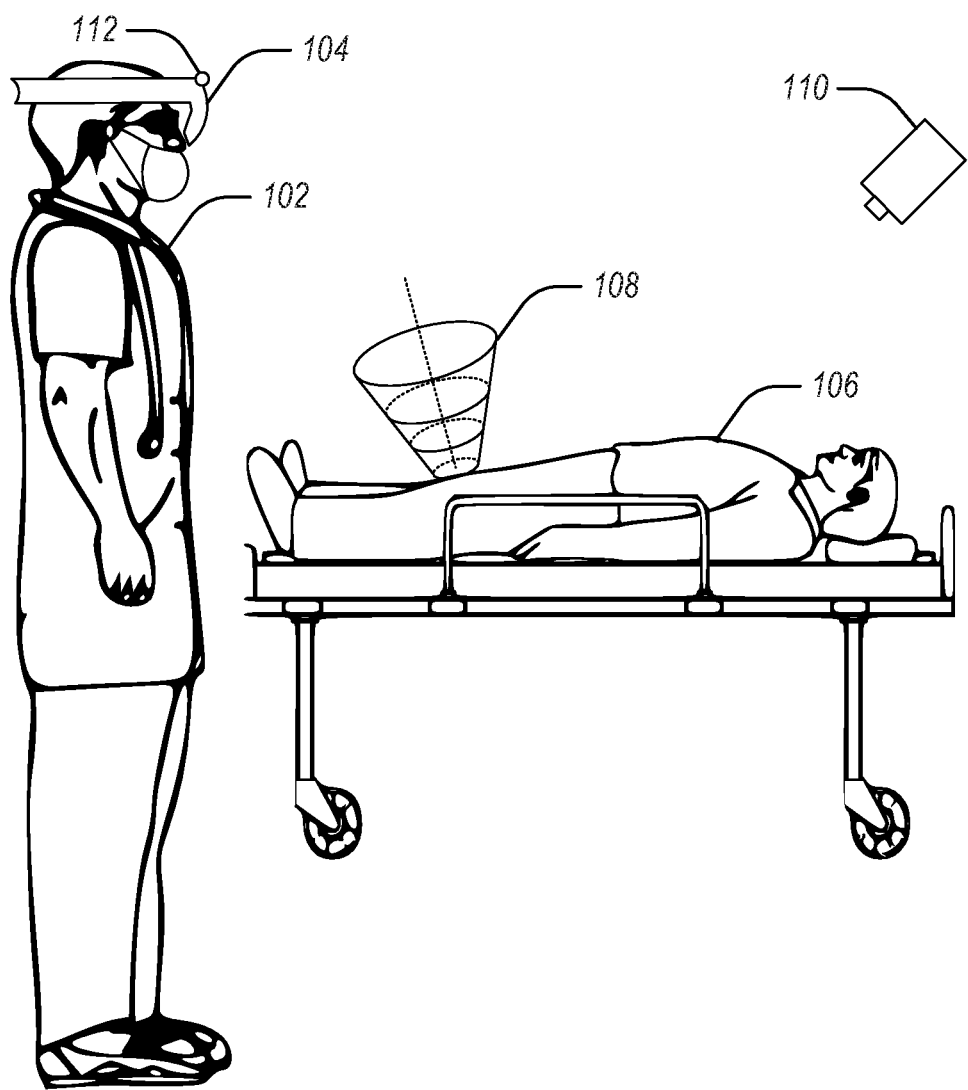
FIG. 1 illustrates a surgical field in accordance with some embodiments.

Systems and methods for using an augmented reality device during a surgical procedure are described herein. The systems and methods herein describe uses for the augmented reality device, such as to display virtual components or representations of real objects overlaid on a real environment. An augmented reality (AR) device allows a user to view displayed virtual objects that appear to be projected into the real environment, which is also visible. AR devices typically include two display lenses or screens, including one for each eye of a user. Light is permitted to pass through the two display lenses such that aspects of the real environment are visible while also projecting light to make virtual elements visible to the user of the AR device.

Described herein are various techniques to use augmented reality to aide in a surgical procedure. The AR devices herein include displays which may provide soft tissue visualization (e.g., a ligament, a tendon, a muscle, etc.) to allow a surgeon to view virtual soft tissue when the actual soft tissue is not visible to the surgeon (e.g., it is blocked by other tissues, a surgical instrument, implant, trial, etc.). AR displays during a minimally invasive surgery may provide visualization of anatomy without the need to expand the incision beyond what is necessary to insert the surgical instruments. The AR displays described herein may display a virtual trial or virtual implant overlaid on a bone. The virtual trial or virtual implant may be modified within the AR display, such as by user input (e.g., a gesture), which may be captured by a camera or a sensor. The modifications may include modifying a fit, size, or location of the virtual trial or implant and providing the modifications to a surgery planning system. Once a virtual trial or implant is determined to be acceptable, a physical trial or implant may be created using the virtual trial or implant as a template. Alternatively, the surgical procedure may be conducted based solely on feedback and adjustments made using the virtual trial implants.

In an example, a surgery planning system may be used to create a surgical plan preoperative. The surgical plan may be modified using the AR displays described herein, and may be modified preoperatively or intraoperatively. For example, an implant or trial size that was selected for the surgical plan may be modified using an AR display. Modifications may be sent to the surgery planning system to output a new surgical plan including the modifications. In another example, when the modifications are made intraoperatively, a new surgical plan may be updated in real time using the surgery planning system.

The AR devices described herein may be used to display a virtual guide for pin placement on a reference location of a bone. The pin placement may include displaying a cone or funnel for alignment and orientation of a pin, which may then be driven into the bone at the reference location based on the virtual guide. The AR devices may provide a virtual representation of part of a surgical instrument, such as a saw blade or other cutting tool (e.g., burr, rasp, reamer) when a portion of the surgical instrument is blocked by a bone, a cut guide, another instrument, or the like. The virtual representation of part of the surgical instrument may appear to be a virtual extension of a visible portion of the surgical instrument. A position or orientation of the virtual representation may be tracked to accurately represent the blocked or hidden portion. The AR devices described herein may display a virtual plane, axis, angle, or rotational information for range of motion testing (e.g., intraoperative range of motion testing).

While some examples and figures described herein relate to specific examples, such as total or partial knee arthroplasty, many of the techniques described herein may be used on hip arthroplasty, shoulder replacement procedures, other orthopedic implant procedures, or the like. The AR devices described herein may display a virtual representation that may replace a physical component, such as a guide, a trial, or the like. In other examples, the AR devices described herein may display virtual representations of hidden or obstructed objects, such as soft tissue, instruments, bones, or the like. The various embodiments described herein may be combined in a unified AR display, such as displaying combinations of one or more guides, trials, hidden or obstructed objects or portions of objects, etc.

FIG. 1 illustrates surgical field 100 in accordance with some embodiments. The surgical field 100 is illustrated in FIG. 1 including a surgeon 102, a patient 106, and may include a camera 110 (or in some examples multiple cameras) or a sensor. The surgeon is wearing an augmented reality (AR) device 104 which may be used to display a virtual object 108 to the surgeon 102. The virtual object 108 may not be visible to others within the surgical field 100 if they are not wearing an AR device. Even if another person is viewing the surgical field with an AR device, the person may not be able to see the virtual object 108 or may be able to see the virtual object 108 in a shared augmented reality with the surgeon 102, or may be able to see a modified version of the virtual object 108 (e.g., according to customizations unique to the surgeon 102 or the person). Augmented reality is explained in more detail below.

Augmented reality is a technology for displaying virtual or "augmented" objects or visual effects overlaid on a real environment. The real environment may include a room or specific area (e.g., the surgical field 100), or may be more general to include the world at large. The virtual aspects overlaid on the real environment may be represented as anchored or in a set position relative to one or more aspects of the real environment. For example, the virtual object 108 may be configured to appear to be resting on a table. An AR system may present virtual aspects that are fixed to a real object without regard to a perspective of a viewer or viewers of the AR system (e.g., the surgeon 102). For example, the virtual object 108 may exist in a room, visible to a viewer of the AR system within the room and not visible to a viewer of the AR system outside the room. The virtual object 108 in the room may be displayed to the viewer outside the room when the viewer enters the room. In this example, the room may act as a real object that the virtual object 108 is fixed to in the AR system.

The AR device 104 may include one or more screens, such as a single screen or two screens (e.g., one per eye of a user). The screens may allow light to pass through the screens such that aspects of the real environment are visible while displaying the virtual object 108. The virtual object 108 may be made visible to the surgeon 102 by projecting light. The virtual object 108 may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object.

A user may see the virtual object 108 presented in an AR system as opaque or as including some level of transparency. In an example, the user may interact with the virtual object 108, such as by moving the virtual object 108 from a first position to a second position. For example, the user may move an object with his or her hand. This may be done in the AR system virtually by determining that the hand has moved into a position coincident or adjacent to the object (e.g., using one or more cameras, which may be mounted on an AR device, such as AR device camera 112 or separate, and which may be static or may be controlled to move, or one or more sensors), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). An AR device 104 may include a camera 112 on the AR device 104 (not to be confused with the camera 110, separate from the AR device 104). The AR device camera 112 or the camera 110 may include an infrared camera, an infrared filter, a visible light filter, a plurality of cameras, a depth camera, etc. The AR device 104 may project virtual items over a representation of a real environment, which may be viewed by a user.

The AR device 104 may be used in the surgical field 100 during a surgical procedure, for example performed by the surgeon 102 on the patient 106. The AR device 104 may project or display virtual objects, such as the virtual object 108 during the surgical procedure to augment the surgeon's vision. The surgeon 102 may control the virtual object 108 using the AR device 104, a remote controller for the AR device 104, or by interacting with the virtual object 108 (e.g., using a hand to "interact" with the virtual object 108 or a gesture recognized by the camera 112 of the AR device 104). The virtual object 108 may augment a surgical tool. For example, the virtual object 108 may appear (to the surgeon 102 viewing the virtual object 108 through the AR device 104) to be coupled with or remain a fixed distance from the surgical tool. In another example, the virtual object 108 may be used to guide the surgical tool, and may appear to be fixed to the patient 106.

Figure 2:
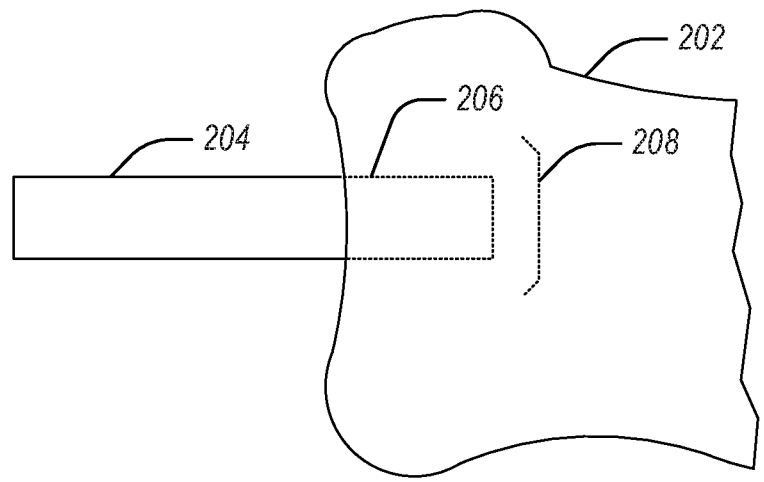
FIG. 2 illustrates an augmented reality display including a hidden surgical instrument in accordance with some embodiments.
Figure 2:
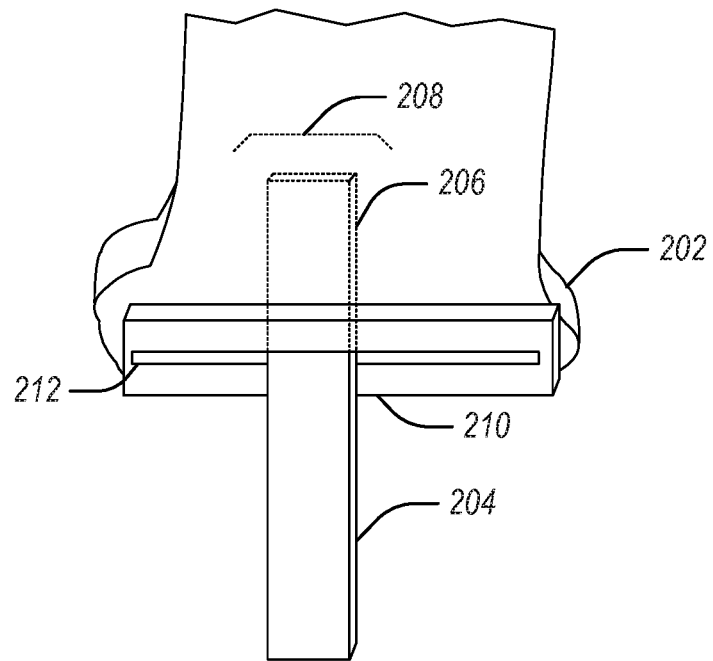

FIG. 2 illustrates augmented reality displays 200A-200B including a partially hidden surgical instrument in accordance with some embodiments. The first AR display 200A illustrates a surgical instrument partially hidden by a bone 202 that is being cut by a surgeon during a surgical procedure. The surgical instrument includes a visible portion 204 and a hidden portion 206, that is hidden within or behind the bone 202.

While the hidden portion 206 of the surgical instrument is not visible to the surgeon, the hidden portion 206 may be tracked. For example, a length of the surgical instrument may be known, and a length or orientation of the visible portion 204 may be identified (e.g., optically) to determine an amount hidden in the hidden portion 206. In another example, an end of the visible portion 204 may be known (e.g., have a sensor or a tracker) and the bone 202 may be fixed or include a sensor or a tracker to determine an entry point of the surgical instrument. In this example, the length or orientation between the sensor or tracker of the surgical instrument and the sensor or tracker of the bone may be calculated, which results in a determination of lengths or orientations of the visible portion 204 and the hidden portion 206. Other techniques may be used to determine lengths or orientations of the visible portion 204 and the hidden portion 206.

An AR device may be used by the surgeon to view the hidden portion 206 during the surgical procedure. The AR device may allow the visible portion 204, the bone 202, or other aspects of a surgical field to be visible through the AR device (e.g., as if the AR device was not used). The hidden portion 206 may be generated and displayed using the AR device. For example, the hidden portion 206 may appear overlaid on the bone 202 when viewed through the AR device. The hidden portion 206 may appear similar to the visible portion 204. The hidden portion 206 may appear connected to the visible portion 204, such that the visible portion 204 and the hidden portion 206 appear to be the surgical instrument (e.g., if it was not inserted into the bone 202). In an example, the hidden portion 206 may be displayed with an augmented virtual effect, such as a color augmentation, flashing light, text, or the like.

When the surgical instrument moves, such as to go deeper or pull out of the bone 202, the amount of the visible portion 204 and the hidden portion 206 may change. The AR device may update the display to accurately reflect the amount of the surgical instrument that is hidden. For example, when the surgical instrument is inserted deeper into the bone 202 to cut additional bone, the hidden portion 206 will increase, and the virtual representation of the hidden portion 206 may increase accordingly. The virtual representation of the hidden portion 206 may thus move and appear or disappear according to the movement and disappearance or appearance of the hidden portion 206 in the bone 202.

In an example, the AR device may optionally display a cut depth 208. For example, the cut depth 208 may be a predetermined maximum depth to cut the bone 202 or a target depth to cut the bone 202. The cut depth 208 may be displayed virtually, such as overlaid on the bone 202 using the AR device. The cut depth 208 may include a plurality of depths for different cuts using the surgical device. When the surgical instrument approaches the cut depth 208, the AR device may display an alert, additional information, or the like. For example, the AR device may display an enlarged view of an area of the bone 202 surrounding or adjacent to the cut depth 208, may include a flashing light, changing color of the cut depth 208 or the hidden portion 206 (or part of the hidden portion 206), a current cut depth of the surgical instrument, etc. The cut depth 208 may be two-dimensional or three-dimensional.

In an example, the surgical instrument may be controlled by a robot (e.g., a robotic arm), which may guide the surgical instrument in making a cut. When controlled by the robot, the hidden portion 206 of the surgical device may be displayed as described above. In an example, when the surgical instrument approaches the cut depth 208, the surgeon may be alerted, the robot may proceed more slowly, the robot may relinquish control of the surgical instrument to the surgeon to finish the cut, the robot may change to a power-assisted mode (e.g., to allow the surgeon to control orientation, direction, and movement of the surgical instrument while providing power to the movement), or the like. The surgeon may monitor the robot making the cut by watching the hidden portion 206 and the cut depth 208. The surgeon may stop the robot, such as if the robot approaches the cut depth 208 too quickly, is at the cut depth 208, or is past the cut depth 208.

In an example, bone 202 may obstruct the surgical instrument when the bone 202 is a tibia and the surgical instrument is a saw blade or other cutting tool (e.g., burr, rasp, reamer). The saw blade or other cutting tool (e.g., burr, rasp, reamer) may make a cut under a tibia plateau of the bone 202, and be shielded from view by the bone 202. The hidden portion 206 may be displayed with the AR device as a "ghost," superimposed on the bone 202. The surgical procedure may be, for example, a total knee arthroplasty. In another example, the surgical instrument may be performing a cut during a revision surgery, the surgical instrument may include a reamer, and the cut depth 208 may include a depth of a reamer cut. The depth cut 208 may include a confirmation of depth of a cut on a resection, such as a tibia cut (e.g., proximal).

The second AR display 200B illustrates a surgical instrument partially hidden by a cut guide 210 and a bone (e.g., the bone 202) that is being cut by a surgeon (using the cut guide 210) during a surgical procedure. The cut guide 210 includes a slot 212 for inserting the surgical instrument. The surgical instrument in the second AR display 200B includes a visible portion 204 and a hidden portion 206, similar to that described above with respect to the first AR display 200A. The second AR display 200B may include the cut depth 208, as described above.

In the second AR display 200B, the hidden portion 206 of the surgical instrument is hidden by both the bone 202 and a portion of the cut guide 210. The hidden portion 206 may be shown as a single virtual component or may have different attributes in the sections hidden behind the bone 202 and the cut guide 210. In an example, the cut guide 210 or the slot 212 may be used to determine a length of the visible portion 204 or the hidden portion 206, such as using sensors, imaging, or the like.

Figure 3:
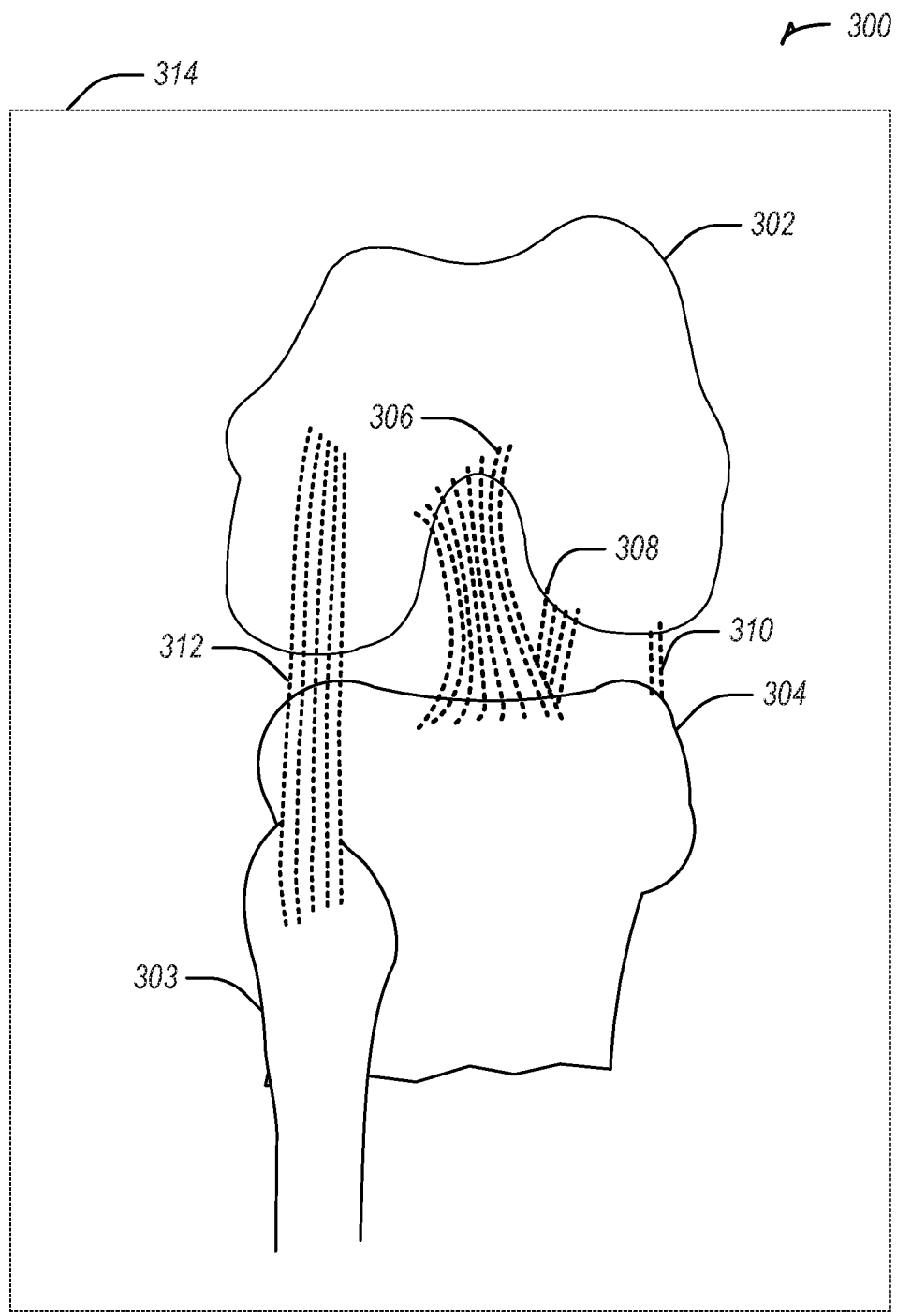
FIG. 3 illustrates an augmented reality display including soft tissue visualization in accordance with some embodiments.

FIG. 3 illustrates an augmented reality display 300 including soft tissue visualization in accordance with some embodiments. The augmented reality display 300 allows a femur bone 302 and a tibia bone 304 to be viewed. The augmented reality display 300 includes virtual representations of soft tissue anatomy, such as virtual representations of an anterior cruciate ligament (ACL) 306, a posterior cruciate ligament (PCL) 308, a lateral collateral ligament (LCL) 312, and a medial collateral ligament (MCL) 310. These virtual ligaments are shown as examples of what virtual representations of soft tissue may be displayed using an AR display. Other examples, such as tendons, muscles, skin, blood vessels, or the like may be displayed virtually using an AR display. The virtual soft tissue shown in the AR display 300 may be shown overlaid in the AR display such that when a device, such as a surgical instrument, or a bone is present, the virtual soft tissue is visible through the AR display, even if the surgical instrument, other device, or bone blocks the actual soft tissue anatomy from display. For example, the patella may block all or part of the actual MCL, so the virtual MCL 310 may be displayed in a manner that appears to be in front of the patella such that a surgeon may see where the actual MCL is located. In a minimally invasive procedure, the augmented reality display 300 may include virtual representations of the femur 302, the tibia 304 and the fibula 303 in addition to the soft tissues described above. The augmented reality display 300 may be overlaid on the surgical field where portions of the bones and/or soft tissue come into and out of actual view, with the augmented reality aspect shifting in coordination with what is actually visible to the surgeon. In an example, a sensor may be used to detect a location of an anatomical feature (e.g., bones, etc.).

In an example, the virtual soft tissue may be visible only when the actual soft tissue is blocked from view (e.g., by detecting the actual soft tissue is blocked using a camera coupled to the AR display 300). The virtual soft tissue may augment the actual soft tissue. For example, the virtual soft tissue may be color coded or include a high contrast color (e.g., ligaments in a first color and tendons in a second, or each ligament may be individually color coded). The virtual soft tissue may outline or highlight the actual soft tissue. In an example, the virtual soft tissue may include a safety zone around the actual soft tissue (e.g., visually represent an area larger than the actual soft tissue) to allow a surgeon to avoid contact with the actual soft tissue with a factor of safety.

In an example, the virtual ligaments 308-312 shown in the AR display 300 may be selected, such as by a surgeon, to activate or deactivate the virtual ligaments from view. The virtual ligaments 308-312 may be selected together, individually, in pairs (e.g., the virtual ACL 306 and the virtual PCL 308, or the virtual LCL 312 and the virtual MCL 310), etc. In another example, the virtual ligaments 308-312 may be displayed according to a procedure being performed by the surgeon. For example, when placing a template during a knee arthroplasty, the virtual ACL 306 may be actively shown to allow the surgeon to avoid contact with the actual ACL. The AR display 300 may be used to show the virtual ACL 306 when inserting an ACL preserving prosthetic, to allow for easier placement.

In an example, the actual soft tissue anatomy to be displayed virtually by the AR display may be captured using imaging, such as a contrast X-ray, an MRI or ultrasound. Once the actual soft tissue anatomy is imaged, a processor may create the virtual soft tissue for display using the AR display 300. The AR display 300 may identify (e.g., with a camera, a sensor, or a user input) a reference point (e.g., on the femur 302), and the virtual soft tissue may then be displayed based on the reference point. In another example, the AR display 300 may show the virtual soft tissue when a device (e.g., a surgical instrument such as a saw blade, burr, rasp, reamer, etc.) approaches or enters a danger zone surrounding the actual soft tissue. The AR display 300 may alert the surgeon, such as by flashing a warning or increasing intensity of light or changing color of the virtual soft tissue when the danger zone is approached or entered.

In an example, the AR display 300 may be used to visualize range of motion aspects of the knee. A plane of motion (e.g., a flexion-extension plane, an abduction-adduction plane 314, etc.) may be virtually displayed for testing a range of motion of the knee (e.g., intraoperatively or postoperatively). The plane of motion may be based on a preoperative plan or detected plane. In another example, the AR display 300 may include varus angle information, valgus angle information, rotational information (e.g., about a virtually displayed axis), or the like in virtual representations. The knee or leg may be rotated or moved to test various aspects of range of motion of the knee or leg, such as along a virtual plane of motion displayed in the AR display 300, along a virtually displayed axis, or according to virtually displayed rotation information. In an example, aspects of the virtually displayed ligaments 306-312 may be displayed to check for laxity when the leg or knee is moved. An angular change in the gap between femur and tibia, such as when a varus or valgus stress is placed on the knee joint may be captured and displayed. Another example includes displaying an anterior distance change between femur and tibia (e.g., natively or with implants in place), such as when an anteriorly directed force is applied to the joint (e.g., anterior drawer test or Lachman's test).

While soft tissue has been described in reference to FIG. 3, other anatomical aspects may be displayed, highlighted, or augmented in an AR display. For example, a bone outline, for example a posterior-lateral corner of the tibia, which is difficult to visualize in standard incisions for total knee arthroplasty procedures, may be displayed. Displaying virtual bone may aid in providing information to a surgeon about when to stop a saw or in sizing of implants, particularly the tibia. Other hidden bone or hard tissue may be displayed in an AR display.

Figure 4:
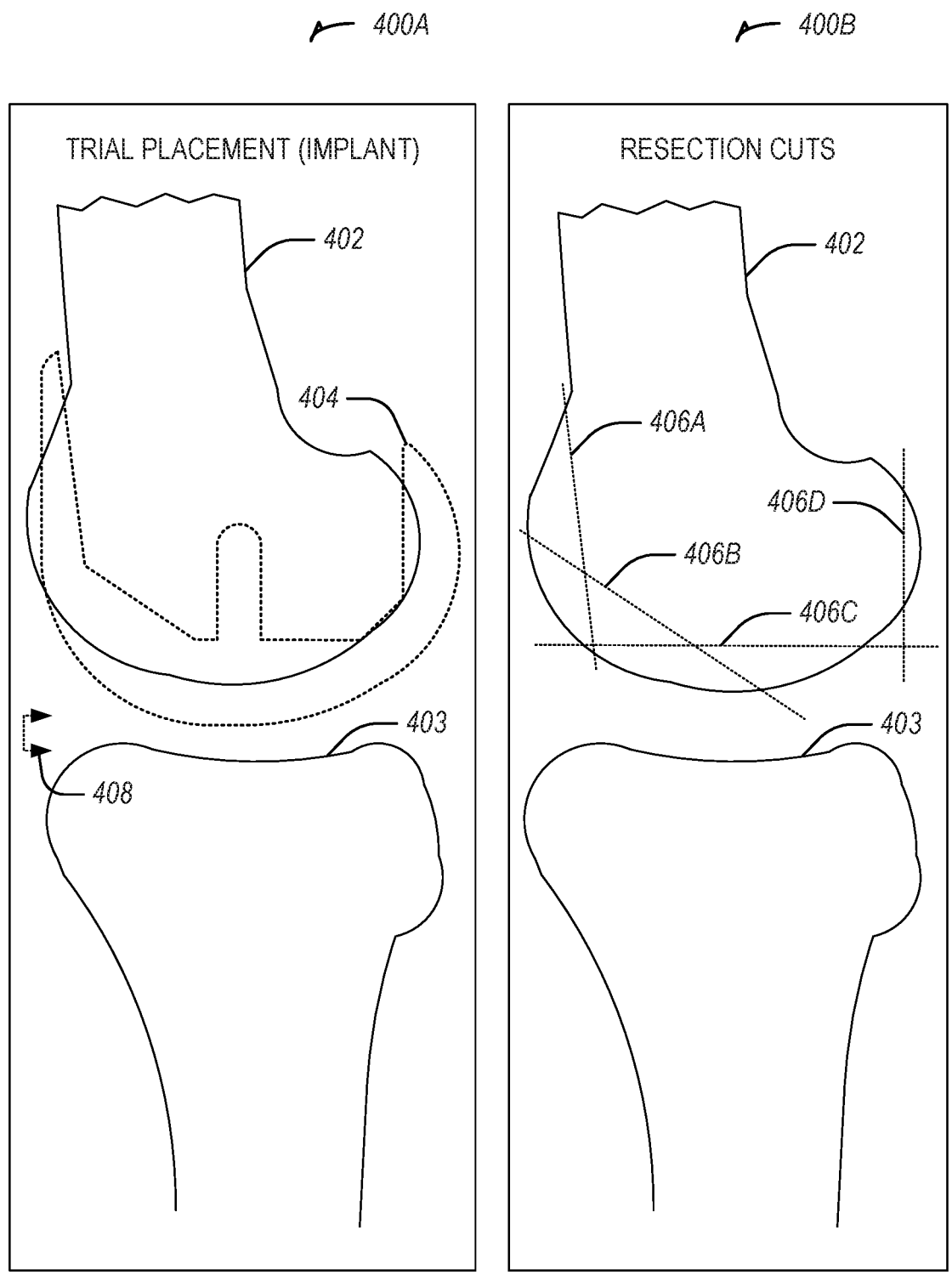
FIG. 4 illustrates augmented reality displays including a virtual planned component in accordance with some embodiments.

FIG. 4 illustrates augmented reality displays 400A-400B including a virtual planned component in accordance with some embodiments. The AR displays 400A-400B allows a patient's femur bone 402 to be visible while displaying virtual components. The femur 402 may be augmented by virtual components in the AR displays 400A-400B, such as an implant or trial 404 in AR display 400A or resection cut guides 406A-406D in AR display 400B.

The AR display 400A illustrates the virtual trial 404 projected on the bone 402. Preoperative determinations may be made regarding the trial to be used in a knee replacement procedure, such as a size or location of the trial. Using the preoperative determinations, a virtual trial 404 may be created (e.g., by a processor) for display in the AR display 400A. The virtual trial 404 may be adjusted, changed, or moved within the AR display 400A based on a displayed fit of the virtual trial 404 with the femur 402. In another example, the virtual trial 404 may be created intraoperatively, such as without preoperative determinations for size or location of a trial. In this example, a size or location of the virtual trial 404 may be determined, and a physical trial may be created using the size or location information of the virtual trial 404.

The AR display 400A may include a virtual representation of a gap 408 between a femoral trial (represented or approximated in the AR display 400A by the virtual trial 404) and a tibia 403. The gap 408 may be displayed with a length value of the gap 408 (e.g., 10 mm or 12 mm). The gap 408 may be adjusted, such as by making changes to the virtual trial 404 (which may represent the actual trial). A proposed bearing thickness option may be displayed, such as based on known resections or locations of tibial or femoral trials. In an example, an anterior distance change between femur and tibia (e.g., natively or with implants in place) may be displayed. When an anteriorly directed force is applied to the joint (e.g., anterior drawer test or Lachman's test), changes in the distance may be displayed. The AR display 400A may project a lighting effect (e.g., a green or red color) based on an assessment of the gap 408 and known minimum implant thickness. For example, when the gap 408 is less than the minimum implant thickness, (e.g., insufficient bone is removed), the gap may show red and if sufficient bone is removed the gap may show green.

In an example, after the actual trial is inserted, a virtual effect may be added to the actual trial, such as by using laser markings on the trial or an augmented virtual outline of the trial. The virtual effect may allow tracking of orientation of the trial without requiring optical navigation or other tracking systems. The virtual effect may be applied to the actual trial with the AR display 400A, such as using a camera (e.g., a visual light camera) on an AR device presenting the AR display 400A.

In an example, virtual markers may be placed on an actual trial and the AR display 400A may guide a surgeon in placing the actual trial, such as according to a preoperative plan. In another example, tracking markers (e.g., non-virtual) may be placed on the actual trial. The femur 402 may include virtual or actual markers to indicate alignment for the actual trial. In an example, the virtual or actual markers on the actual trial may align with the virtual or actual markers on the femur 402 to place the trial.

The AR display 400B illustrates virtual resection cuts 406A-406D to be made on the femur 402 such that a trial or implant may be placed. The virtual resection cuts 406A-406D may be shown virtually as lines or planes and may be moved by a surgeon operating an AR device that displays the AR display 400B and allows the femur 402 to be viewed. One or more of the virtual resection cuts 406A-406D may be displayed virtually in place of a cut guide or a cut block. The surgeon may make cuts with a surgical saw along the virtual resection cuts 406A-406D to prepare the femur 402 to receive an implant. The virtual resection cuts 406A-406D may be created based on a preoperative plan. In an example, once a cut is performed, the corresponding virtual resection cut may be removed or may be modified, such as to suggest an additional cut to fit a trial. The virtual trial 404 of AR display 400A and the virtual resection cuts 406A-406D AR display 400B may be interchanged, displayed concurrently, or modified, such as based on a user input. A virtual cut guide, virtual trial, or virtual implant may be used for placing an implant on the tibia 403 or other bone during an implant procedure (e.g., shoulder replacement, hip replacement, etc.). The virtual resection cuts 406A-406D may be used to monitor a robot performing cuts.

Figure 5:
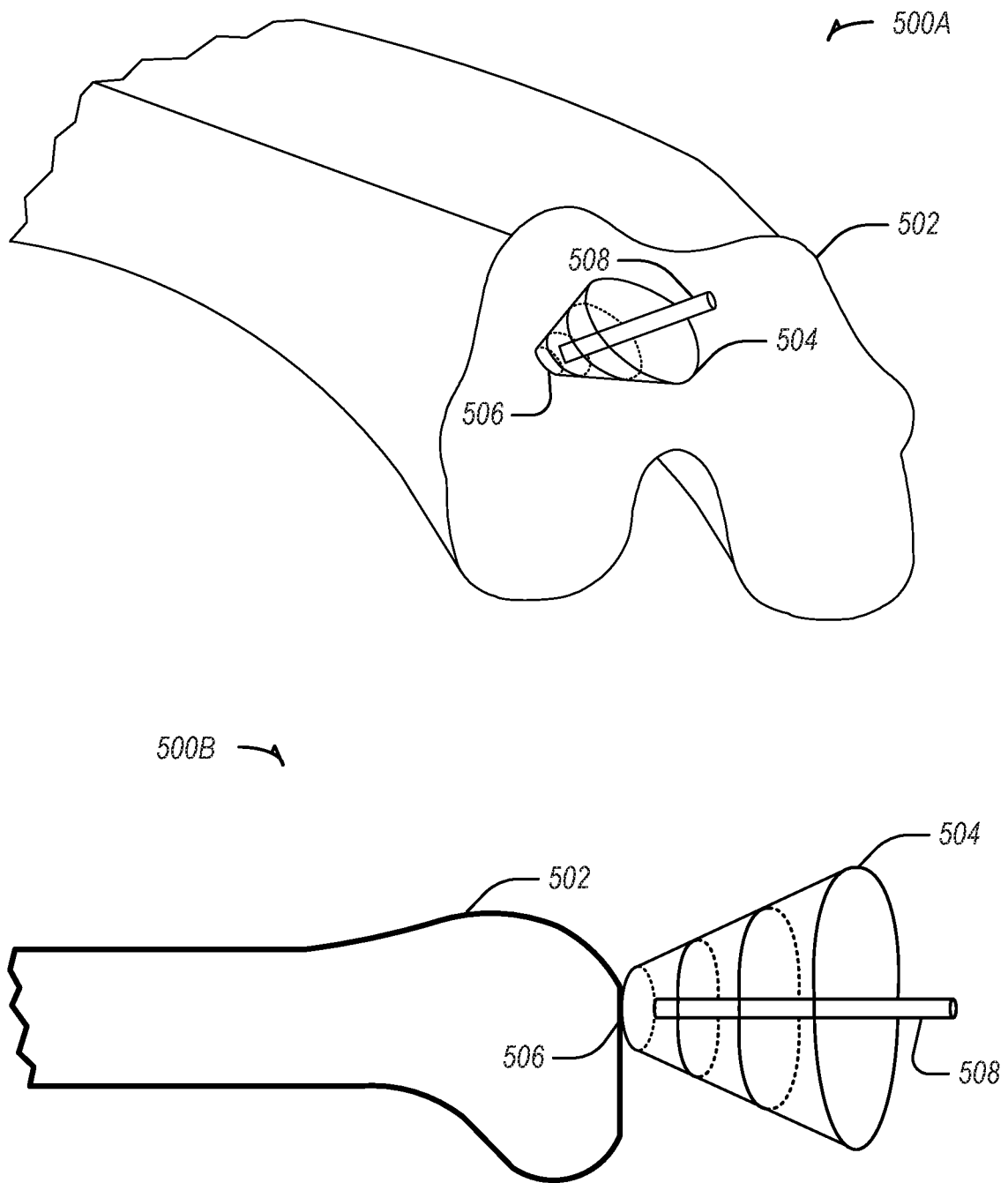
FIG. 5 illustrates augmented reality displays including an example guide for pin placement in accordance with some embodiments.

FIG. 5 illustrates augmented reality displays 500A-500B including an example virtual guide 504 for pin placement in accordance with some embodiments. The virtual guide 504 is shown in relation to a bone 502 for placing a pin 508 at a reference location 506 on the bone 502. The first AR display 500A illustrates a perspective view of the bone 502 and the second AR display 500B illustrates a side view of the bone 502.

In an example, the virtual guide 504 may appear as a funnel or cone shape to guide a surgeon in placing the pin 508 at the reference location 506. The virtual guide 504 may taper or narrow down to the reference location 506 on a surface of the bone 502, while appearing to start off the surface of the bone 502. The virtual guide 504 may include a visual identification of orientation of the pin 508. For example, the virtual guide 504 may be color coded according to proximity of the pin 508 to a portion of the virtual guide 504 (e.g., if the pin 508 is angled, a quadrant or other portion of the virtual guide 504 may change color or light up. The virtual guide 504 may be created by an AR system based on preoperative planning. The virtual guide 504 may be three dimensional and allow for instrumentless pin placement using AR guidance in three dimensions. In another example, the virtual guide 504 may be used to guide a punch or other instrument, such as an instrument with a linear action and that may have a position in multiple degrees of freedom.

AR guides similar to those illustrated in FIG. 5 may also be generated to guide drilling or cutting procedures. Similar guides can be used to guide cut angles or locations for a surgical saw, or other cutting tool (e.g., burr, rasp, reamer), for example.

Figure 6:
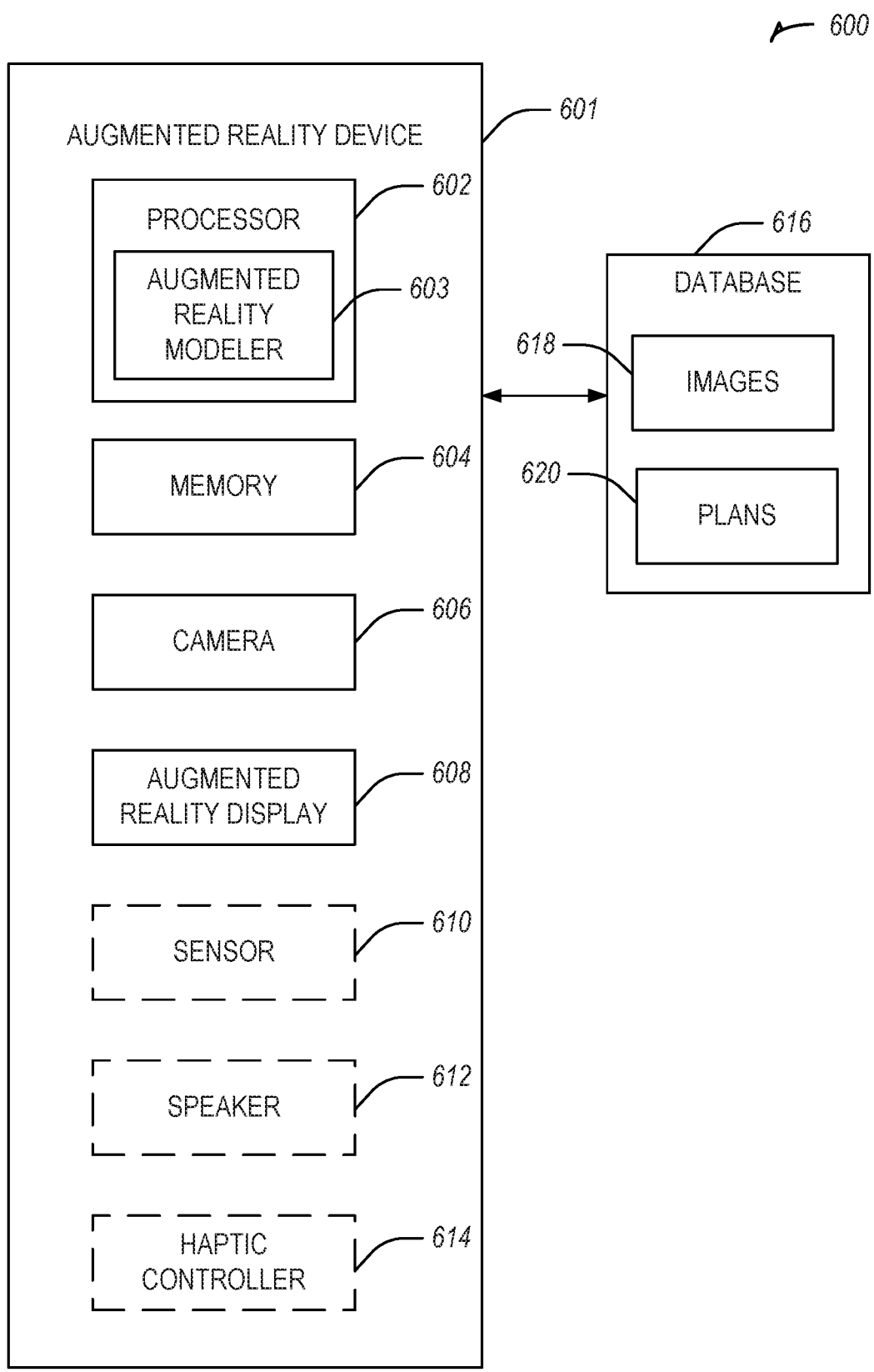
FIG. 6 illustrates a system for using an augmented reality device during a surgical procedure in accordance with some embodiments.

FIG. 6 illustrates a system 600 for using an augmented reality device during a surgical procedure in accordance with some embodiments. The system includes an augmented reality device 601 that may be in communication with a database 616. The augmented reality device 601 includes a processor 602, memory 604, an AR display 608, and a camera 606. The augmented reality device 601 may include a sensor 610, a speaker 612, or a haptic controller 614. The database 616 may include image storage 618 or preoperative plan storage 620. In an example, the augmented reality device 601 may be a HoloLens manufactured by Microsoft of Redmond, Wash.

The processor 602 of the augmented reality device 601 includes an augmented reality modeler 603. The augmented reality modeler 603 may be used by the processor 602 to create the augmented reality environment. For example, the augmented reality modeler 603 may receive dimensions of a room, such as from the camera 606 or sensor 610, and create the augmented reality environment to fit within the physical structure of the room. In another example, physical objects may be present in the room and the augmented reality modeler 603 may use the physical objects to present virtual objects in the augmented reality environment. For example, the augmented reality modeler 603 may use or detect a table present in the room and present a virtual object as resting on the table. The AR display 608 may display the AR environment overlaid on a real environment. The display 608 may show a virtual object, using the AR device 601, such as in a fixed position in the AR environment.

The augmented reality device 601 may include a sensor 610, such as an infrared sensor. The camera 606 or the sensor 610 may be used to detect movement, such as a gesture by a surgeon or other user, that may be interpreted by the processor 602 as attempted or intended interaction by the user with the virtual target. The processor 602 may identify an object in a real environment, such as through processing information received using the camera 606.

The AR display 608, for example during a surgical procedure, may present, such as within a surgical field while permitting the surgical field to be viewed through the augmented reality display, a virtual feature corresponding to a physical feature hidden by an anatomical aspect of a patient. The virtual feature may have a virtual position or orientation corresponding to a first physical position or orientation of the physical feature. For example, the physical feature may include soft tissue, and the virtual feature may include virtual soft tissue, which may be superimposed on the anatomical aspect of the patient. The surgical procedure may include a knee arthroplasty (e.g., total or partial). The virtual soft tissue may include one or more ligaments, such as an ACL, PCL, MCL, or LCL, to avoid when placing a template during the surgical procedure. In an example, a relative physical position or orientation of the physical feature (e.g., a ligament) to the anatomical aspect may be determined preoperatively, such as using an x-ray, an MRI, or ultrasound.

In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In an example, the physical feature is a saw blade, the virtual feature is a virtual saw blade, and the anatomical aspect is a bone of the patient. The saw blade may be hidden by the bone, such as a tibia plateau while performing a cut, and the virtual saw blade may be shown overlaid on the tibia plateau to allow a virtual view of the hidden portion of the saw blade. The AR display 608 may display a virtual indication of a cut completion location for the saw blade, in an example. The AR display 608 may display a warning that the hidden physical feature is approaching or has crossed a threshold safety zone. The physical feature may be a cutting tool (e.g., burr, rasp, reamer), and the virtual feature may be a virtual representation of the cutting tool.

The camera 606 may detect movement of the anatomical aspect or the physical feature. The processor 602 may be used to cause the virtual feature to move such that the virtual position and orientation of the virtual feature correspond to a second physical position and orientation of the physical feature. Causing the virtual feature to move may be performed in response to the detected movement of the anatomical aspect or the physical feature. The speaker 612 may be used to play an audible warning that the hidden physical feature is approaching or has crossed a threshold safety zone.

The AR display 608, for example during a surgical procedure, may project a virtual representation of an aspect of a preoperative plan, such as at a planned location within a surgical field while permitting the surgical field to be viewed through the AR display 608. In an example, the aspect of the preoperative plan may include a virtual representation of a trial or an implant. The surgical component may include the trial or the implant. The AR display 608 may present a virtual representation of a gap thickness, such as the extension-flexion gap thickness. The trial may include laser markings or other markings for tracking an orientation of the trial. The AR display 608 may project a proposed bearing thickness option, such as based on known resections or preoperatively planned resections, or a location of a trial or implant. In an example, the aspect may include a virtual guide. The virtual guide may include a funnel or cone or funneling cone, such as for pin placement. The funneling cone may narrow down to a pin point (e.g., reference location) on a bone, such as a femur.

The camera 606 may capture an image of a surgical component within the surgical field. The camera 606 may detect a gesture (or capture a series of images and send the series of images to the processor 602 to detect the gesture), such as from a surgeon. The gesture may change a preoperative plan, move a virtual component, play or pause a video, change to a next step of a surgical plan, add or subtract virtual components, or the like. The processor 602 may be used to compare a location of the surgical component within the surgical field from the captured image to another location, such as the planned location within the preoperative plan. The processor 602 may output results of the comparison, such as for display on the AR display 608.

In an example, in response to the results of the comparison being output by the processor 608, the AR display 608 may present a visual indication of the results. The speaker 612 may play an audible alert or indication of the results, such as in response to the results of the comparison being output by the processor 602. The haptic controller 614 may cause a vibration to indicate the results, such as in response to the results of the comparison being output by the processor 602. In an example, the preoperative plan includes a range of motion, the virtual representation of the aspect of the preoperative plan includes a virtual range of motion visual effect, and the surgical component includes a patient limb to be moved through the range of motion.

In an example, the aspect of the preoperative plan includes a virtual representation of an implant and the surgical component may be the implant. To compare the location of the surgical component to the planned location, the processor 602 may determine a degree of overlap between the surgical component and the virtual representation. The results of the comparison may include the degree of overlap. In an example, such as in response to determining the degree of overlap is above a threshold, the AR display 608 may project the virtual representation in a color, such as green. In another example, such as in response to determining the degree of overlap is below the threshold, the AR display may project the virtual representation in a different color, such as red.

Figure 7:
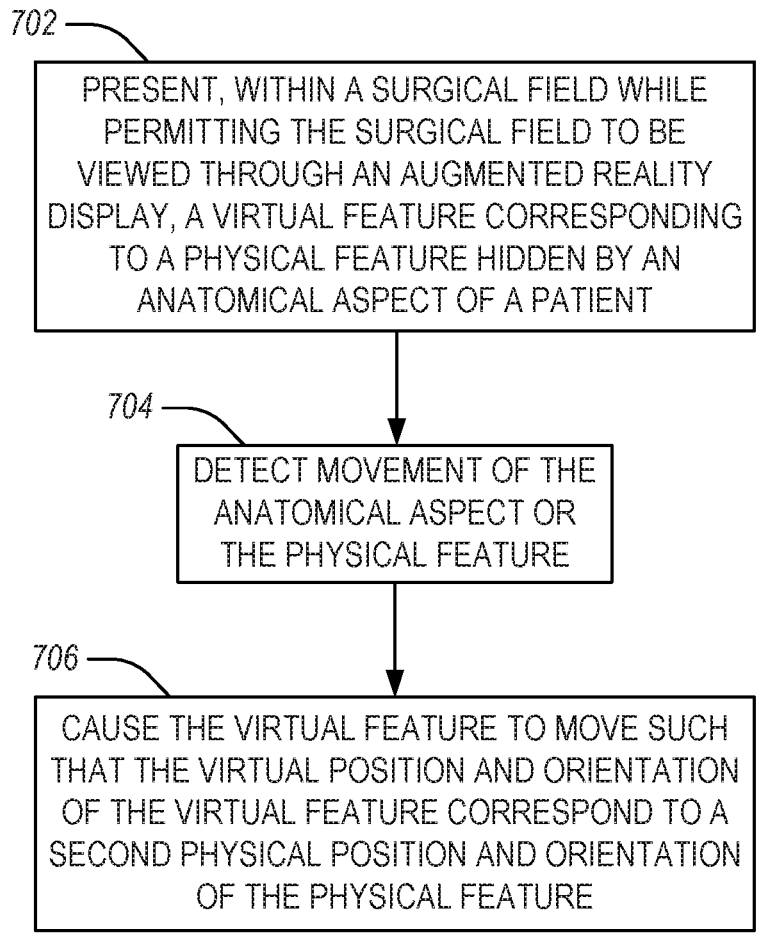
FIG. 7 illustrates a flow chart showing a technique for using an augmented reality device during a surgical procedure to present a hidden feature in accordance with some embodiments.

FIG. 7 illustrates a flow chart showing a technique 700 for using an augmented reality device during a surgical procedure to present a hidden feature in accordance with some embodiments. The technique 700 includes an operation 702 to present, within a surgical field while permitting the surgical field to be viewed through an augmented reality display, a virtual feature corresponding to a physical feature hidden by an anatomical aspect of a patient. The virtual feature may be presented using an AR display of the AR device. The virtual feature may have a virtual position or orientation corresponding to a first physical position or orientation of the physical feature.

In an example, presenting the virtual feature includes presenting the virtual feature at the virtual position or orientation of the virtual feature at an offset from the first physical position or orientation of the physical feature. In another example, presenting the virtual feature includes presenting a virtual representation of soft tissue superimposed on the anatomical aspect of the patient. The virtual feature may be presented during a total or partial knee arthroplasty (or shoulder replacement or hip arthroplasty). One or more virtual ligaments may be presented in the AR display, to allow a surgeon to avoid the actual ligaments when placing a template, trial, implant during a surgical procedure, or when resecting tissue, such as removing bone. The technique 700 may include determining a relative physical position and orientation of the physical feature to the anatomical aspect, such as preoperatively using an x-ray or an MRI. Presenting the virtual feature may include presenting a virtual saw blade corresponding to a saw blade, and wherein the anatomical aspect is a bone of the patient. The AR display may display a virtual indication of a cut completion location for the saw blade. The technique 700 may include displaying, using the AR display, a warning that the hidden physical feature is approaching or has crossed a threshold safety zone. An audible warning may be played indicating that the hidden feature is approaching or has crossed a threshold safety zone. In some examples, displaying the virtual feature may include calculating an approximate location of the virtual feature in reference to portion of adjacent anatomy, such as approximating positions of soft tissue based on known positions of adjacent bones. In these examples, pre-operative imaging allows for creation of starting 3D models of anatomy surrounding a joint, such as the knee, with approximations generated based on movement of adjacent bones from known locations in the starting 3D model.

The technique 700 includes an operation 704 to detect movement of the anatomical aspect or the physical feature, such as using a sensor. The technique 700 includes an operation 706 to cause, such as with a processor, the virtual feature to move such that the virtual position or orientation of the virtual feature correspond to a second physical position or orientation of the physical feature, for example, in response to the detected movement of the anatomical aspect or the physical feature.

Figure 8:
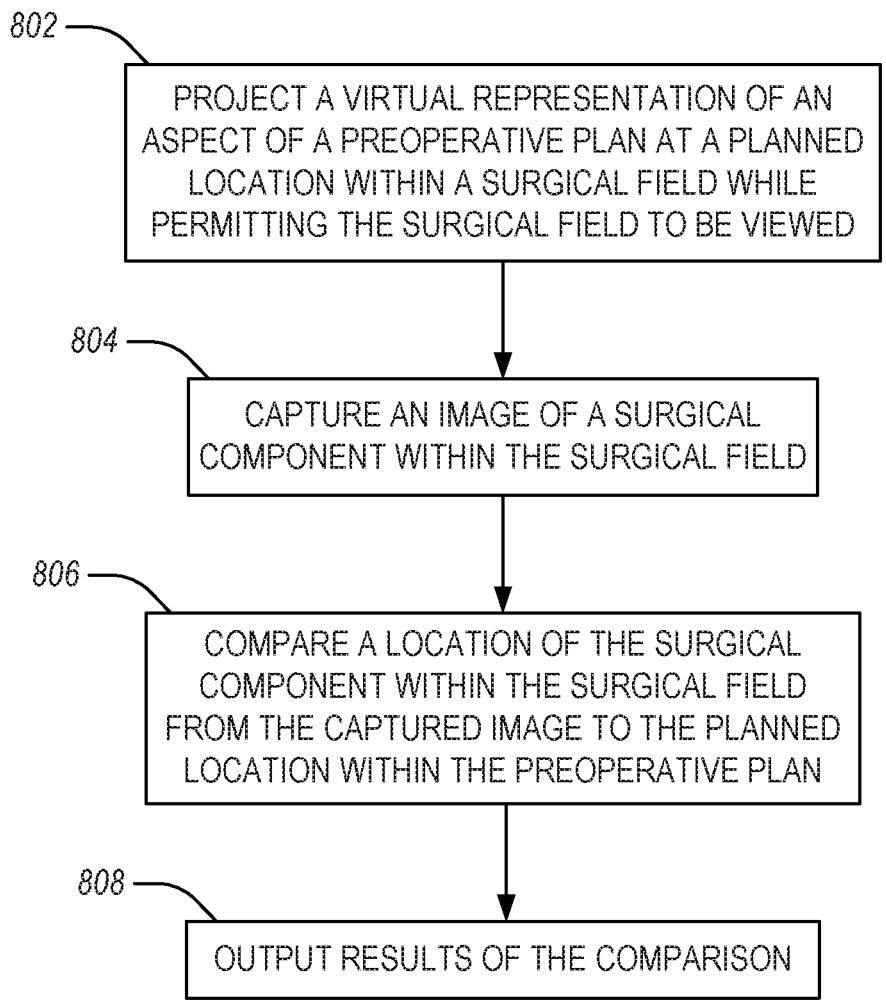
FIG. 8 illustrates a flow chart showing a technique for using an augmented reality device during a surgical procedure to project an aspect of a preoperative plan in accordance with some embodiments.

FIG. 8 illustrates a flow chart showing a technique 800 for using an augmented reality device during a surgical procedure to project an aspect of a preoperative plan in accordance with some embodiments. The technique 800 includes an operation 802 to project, using an AR display, a virtual representation of an aspect of a preoperative plan at a planned location within a surgical field while permitting the surgical field to be viewed. In an example, the aspect of the preoperative plan includes a virtual representation of an implant. The surgical component may be the implant. When comparing the location of the surgical component to the planned location, the technique 800 may include determining a degree of overlap between the surgical component and the virtual representation and wherein the results of the comparison include the degree of overlap. The technique 800 may include projecting, using the AR display, the virtual representation in a first color (e.g., green), for example in response to determining the degree of overlap is above a threshold. The technique 800 may include projecting, using the AR display, the virtual representation in a second color (e.g., red) in response to determining the degree of overlap is below the threshold.

The preoperative plan may include one or more planes, such as those defining an anatomical or a mechanical axis of a joint. The one or more planes may be determined preoperatively and displayed using the AR display intraoperatively. In an example, the one or more planes may be used for range of motion testing intraoperatively, such as to guide a range of motion test. In an example, the preoperative plan may include a virtual limb alignment, for example, mechanical or anatomic, such as based on one or more bony landmarks.

In an example, the aspect of the preoperative plan includes a virtual representation of a trial and wherein the surgical component is the trial. The technique 800 may include presenting, using the augmented reality display, a virtual representation of an extension or flexion gap thickness. In an example, a change in gap, such as when under a varus or valgus load, may be displayed as an angle or linear measurement. The actual trial may include laser or other markings for tracking an orientation of the trial. The technique 800 may include projecting, using the augmented reality display, a proposed bearing thickness option based on known resections and locations of the actual trial.

The technique 800 includes an operation 804 to capture an image of a surgical component within the surgical field, such as by using a sensor. The technique 800 includes an operation 806 to compare a location of the surgical component within the surgical field from the captured image to the planned location within the preoperative plan. The technique 800 includes an operation 808 to output results of the comparison.

The aspect may include a virtual guide. The virtual guide may include a funnel, a cone, or a funneling cone, such as for placement of a pin. The funneling cone may narrow down to a reference point on a bone, such as a femur or a tibia, for placing the pin in the bone. The technique 800 may include detecting a gesture from a surgeon to change the preoperative plan. In an example, the technique 800 includes presenting, using the augmented reality display, a visual indication of the results, such as in response to the results of the comparison being output by the processor. The technique 800 may include playing an audible alert or indication of the results, such as in response to the results of the comparison being output. In an example, the technique 800 includes causing a vibration to indicate the results, such as in response to the results of the comparison being output.

Figure 9:
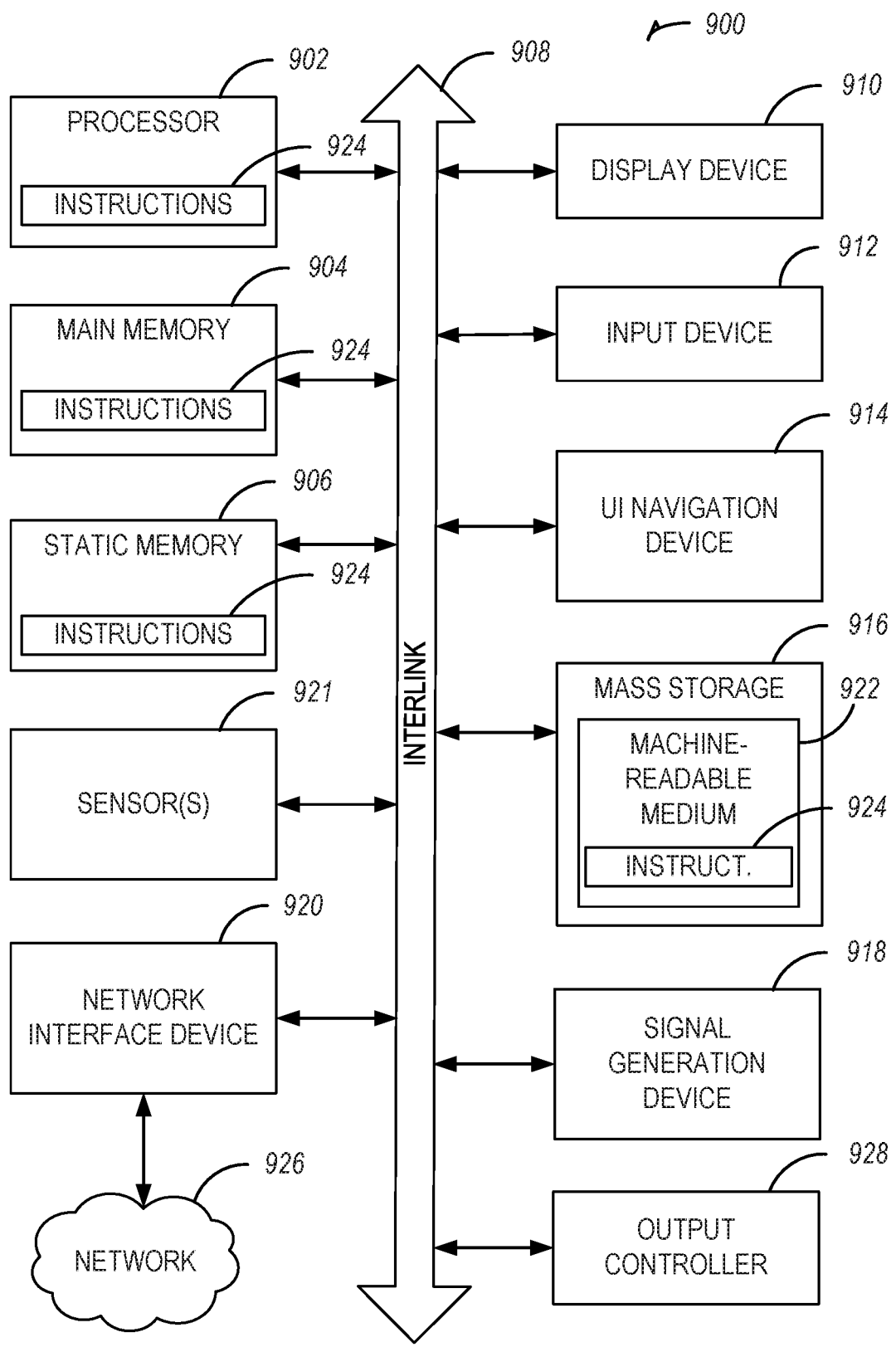
FIG. 9 illustrates generally an example of a block diagram of a machine upon which any one or more of the techniques discussed herein may perform in accordance with some embodiments.

FIG. 9 illustrates generally an example of a block diagram of a machine 900 upon which any one or more of the techniques (e.g., methodologies) discussed herein may perform in accordance with some embodiments. In alternative embodiments, the machine 900 may operate as a standalone device or may be connected (e.g., networked) to other machines. In a networked deployment, the machine 900 may operate in the capacity of a server machine, a client machine, or both in server-client network environments. The machine 900 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910, an alphanumeric input device 912 (e.g., a keyboard), and a user interface (UI) navigation device 914 (e.g., a mouse). In an example, the display unit 910, alphanumeric input device 912 and UI navigation device 914 may be a touch screen display. The display unit 910 may include goggles, glasses, or other AR or VR display components. For example, the display unit may be worn on a head of a user and may provide a heads-up-display to the user. The alphanumeric input device 912 may include a virtual keyboard (e.g., a keyboard displayed virtually in a VR or AR setting.

The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensor. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices.

The storage device 916 may include a machine readable medium 922 that is non-transitory on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine readable medium 922 is illustrated as a single medium, the term "machine readable medium" may include a single medium or multiple media (e.g., a centralized or distributed database, or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 924 may further be transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 920 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is an augmented reality device for use during a surgical procedure comprising: an augmented reality display to present, within a surgical field while permitting the surgical field to be viewed through the augmented reality display, a virtual feature corresponding to a physical feature hidden by an anatomical aspect of a patient, the virtual feature having a virtual position and orientation corresponding to a first physical position and orientation of the physical feature; a sensor to detect movement of the anatomical aspect or the physical feature; and a processor to, in response to the detected movement of the anatomical aspect or the physical feature, cause the virtual feature to move such that the virtual position and orientation of the virtual feature correspond to a second physical position and orientation of the physical feature.

In Example 2, the subject matter of Example 1 optionally includes wherein the virtual position and orientation of the virtual feature includes an offset from the first physical position and orientation of the physical feature.

In Example 3, the subject matter of Example 2 optionally includes wherein the offset is a predetermined distance from the augmented reality display.

In Example 4, the subject matter of any one or more of Examples 2-3 optionally include wherein the offset is a relative distance from the augmented reality display to the anatomical aspect.

In Example 5, the subject matter of any one or more of Examples 1-4 optionally include wherein the physical feature includes soft tissue, and the virtual feature includes virtual soft tissue, superimposed on the anatomical aspect of the patient.

In Example 6, the subject matter of Example 5 optionally includes wherein the surgical procedure is a total knee arthroplasty and wherein the virtual soft tissue includes ligaments to avoid when placing a template during the total knee arthroplasty.

In Example 7, the subject matter of any one or more of Examples 5-6 optionally include wherein a relative physical position and orientation of the physical feature to the anatomical aspect is determined preoperatively using an x-ray or an MRI.

In Example 8, the subject matter of any one or more of Examples 1-7 optionally include wherein the physical feature is a saw blade, the virtual feature is a virtual saw blade, and the anatomical aspect is a bone of the patient.

In Example 9, the subject matter of Example 8 optionally includes wherein the saw blade is hidden under a tibia plateau of the bone while performing a cut.

In Example 10, the subject matter of any one or more of Examples 8-9 optionally include wherein the augmented reality display is further to display a virtual indication of a cut completion location for the saw blade.

In Example 11, the subject matter of any one or more of Examples 1-10 optionally include wherein the augmented reality display is further to display a warning that the hidden physical feature is approaching or has crossed a threshold safety zone.

In Example 12, the subject matter of any one or more of Examples 1-11 optionally include a speaker to play an audible warning that the hidden physical feature is approaching or has crossed a threshold safety zone.

In Example 13, the subject matter of any one or more of Examples 1-12 optionally include a second camera to detect aspects of the surgical field to improve display precision of the virtual feature or improve tracking precision of elements in the surgical field.

Example 14 is a method for using an augmented reality device during a surgical procedure comprising: presenting, using an augmented reality display of the augmented reality device, within a surgical field while permitting the surgical field to be viewed through the augmented reality display, a virtual feature corresponding to a physical feature hidden by an anatomical aspect of a patient, the virtual feature having a virtual position and orientation corresponding to a first physical position and orientation of the physical feature; detecting, using a sensor, movement of the anatomical aspect or the physical feature; and in response to the detected movement of the anatomical aspect or the physical feature, causing, using a processor, the virtual feature to move such that the virtual position and orientation of the virtual feature correspond to a second physical position and orientation of the physical feature.

In Example 15, the subject matter of Example 14 optionally includes wherein presenting the virtual feature includes presenting the virtual feature at the virtual position and orientation of the virtual feature at an offset from the first physical position and orientation of the physical feature.

In Example 16, the subject matter of any one or more of Examples 14-15 optionally include wherein presenting the virtual feature includes presenting a virtual representation of soft tissue superimposed on the anatomical aspect of the patient.

In Example 17, the subject matter of Example 16 optionally includes wherein presenting the virtual feature includes presenting the virtual feature during a total knee arthroplasty and presenting ligaments to avoid when placing a template during the total knee arthroplasty.

In Example 18, the subject matter of any one or more of Examples 16-17 optionally include determining a relative physical position and orientation of the physical feature to the anatomical aspect preoperatively using an x-ray or an MRI.

In Example 19, the subject matter of any one or more of Examples 14-18 optionally include wherein presenting the virtual feature includes presenting a virtual saw blade corresponding to a saw blade, and wherein the anatomical aspect is a bone of the patient.

In Example 20, the subject matter of Example 19 optionally includes displaying a virtual indication of a cut completion location for the saw blade using the augmented reality display.

In Example 21, the subject matter of any one or more of Examples 14-20 optionally include displaying a warning that the hidden physical feature is approaching or has crossed a threshold safety zone using the augmented reality display.

In Example 22, the subject matter of any one or more of Examples 14-21 optionally include playing an audible warning that the hidden physical feature is approaching or has crossed a threshold safety zone.

Example 23 is at least one machine readable medium including instructions for using an augmented reality device during a surgical procedure, which when executed by a machine, cause the machine to: present, for display on an augmented reality display, within a surgical field while permitting the surgical field to be viewed through the augmented reality display, a virtual feature corresponding to a physical feature hidden by an anatomical aspect of a patient, the virtual feature having a virtual position and orientation corresponding to a first physical position and orientation of the physical feature; detect, from images captured by a sensor, movement of the anatomical aspect or the physical feature; and in response to the detected movement of the anatomical aspect or the physical feature, cause the virtual feature to move such that the virtual position and orientation of the virtual feature correspond to a second physical position and orientation of the physical feature.

In Example 24, the subject matter of Example 23 optionally includes wherein the instructions to present the virtual feature include instructions to present the virtual feature at the virtual position and orientation of the virtual feature at an offset from the first physical position and orientation of the physical feature.

In Example 25, the subject matter of any one or more of Examples 23-24 optionally include wherein the instructions to present the virtual feature include instructions to present a virtual representation of soft tissue superimposed on the anatomical aspect of the patient.

In Example 26, the subject matter of Example 25 optionally includes wherein the instructions to present the virtual feature includes instructions to present the virtual feature during a total knee arthroplasty and presenting ligaments to avoid when placing a template during the total knee arthroplasty.

In Example 27, the subject matter of any one or more of Examples 25-26 optionally include instructions to determine a relative physical position and orientation of the physical feature to the anatomical aspect preoperatively using an x-ray or an MRI.

In Example 28, the subject matter of any one or more of Examples 23-27 optionally include wherein the instructions to present the virtual feature include instructions to present a virtual saw blade corresponding to a saw blade, and wherein the anatomical aspect is a bone of the patient.

In Example 29, the subject matter of Example 28 optionally includes instructions to display a virtual indication of a cut completion location for the saw blade using the augmented reality display.

In Example 30, the subject matter of any one or more of Examples 23-29 optionally include instructions to display a warning that the hidden physical feature is approaching or has crossed a threshold safety zone using the augmented reality display.

In Example 31, the subject matter of any one or more of Examples 23-30 optionally include instructions to play an audible warning that the hidden physical feature is approaching or has crossed a threshold safety zone.

Example 32 is an augmented reality device for use during a surgical procedure comprising: an augmented reality display to project a virtual representation of an aspect of a preoperative plan at a planned location within a surgical field while permitting the surgical field to be viewed through the augmented reality display; a sensor to capture location and orientation information of a surgical component within the surgical field; and a processor to: compare the location of the surgical component within the surgical field to the planned location within the preoperative plan; and output results of the comparison.

In Example 33, the subject matter of Example 32 optionally includes wherein the aspect of the preoperative plan includes a virtual representation of an implant and wherein the surgical component is the implant.

In Example 34, the subject matter of Example 33 optionally includes wherein to compare the location of the surgical component to the planned location, the processor is to determine a degree of overlap between the surgical component and the virtual representation and wherein the results of the comparison include the degree of overlap.

In Example 35, the subject matter of Example 34 optionally includes wherein, in response to determining the degree of overlap is above a threshold, the augmented reality display is further to project the virtual representation in a green color, and in response to determining the degree of overlap is below the threshold, the augmented reality display is further to project the virtual representation in a red color.

In Example 36, the subject matter of any one or more of Examples 32-35 optionally include wherein the aspect of the preoperative plan includes a virtual representation of a trial and wherein the surgical component is the trial.

In Example 37, the subject matter of Example 36 optionally includes wherein the augmented reality display is further to present a virtual representation of an extension-flexion gap thickness.

In Example 38, the subject matter of any one or more of Examples 36-37 optionally include wherein the trial includes laser markings for tracking an orientation of the trial.

In Example 39, the subject matter of any one or more of Examples 36-38 optionally include wherein the augmented reality display is further to project a proposed bearing thickness option based on known resections and locations of the trial.

In Example 40, the subject matter of any one or more of Examples 32-39 optionally include wherein the aspect includes a virtual guide.

In Example 41, the subject matter of Example 40 optionally includes wherein the virtual guide includes a funneling cone for pin placement.

In Example 42, the subject matter of Example 41 optionally includes wherein the funneling cone narrows down to a pin point on a femur.

In Example 43, the subject matter of any one or more of Examples 32-42 optionally include wherein the sensor is further to detect a gesture from a surgeon to change the preoperative plan.

In Example 44, the subject matter of any one or more of Examples 32-43 optionally include wherein, in response to the results of the comparison being output by the processor, the augmented reality display is further to present a visual indication of the results.

In Example 45, the subject matter of any one or more of Examples 32-44 optionally include a speaker to, in response to the results of the comparison being output by the processor, play an audible alert or indication of the results.

In Example 46, the subject matter of any one or more of Examples 32-45 optionally include a haptic controller to, in response to the results of the comparison being output by the processor, cause a vibration to indicate the results.

In Example 47, the subject matter of any one or more of Examples 32-46 optionally include wherein the preoperative plan includes a range of motion, the virtual representation of the aspect of the preoperative plan includes a virtual range of motion visual effect, and the surgical component includes a patient limb to be moved through the range of motion.

In Example 48, the subject matter of any one or more of Examples 32-47 optionally include wherein the sensor includes a camera to capture an image of a surgical component within the surgical field.

Example 49 is a method for using an augmented reality device during a surgical procedure comprising: projecting, using an augmented reality display of the augmented reality device, a virtual representation of an aspect of a preoperative plan at a planned location within a surgical field while permitting the surgical field to be viewed through the augmented reality display; capturing a location and orientation of a surgical component within the surgical field using a tracking device; comparing, using a processor, the location of the surgical component within the surgical field to the planned location within the preoperative plan; and outputting results of the comparison.

In Example 50, the subject matter of Example 49 optionally includes wherein the aspect of the preoperative plan includes a virtual representation of an implant and wherein the surgical component is the implant, and wherein comparing the location of the surgical component to the planned location includes determining a degree of overlap between the surgical component and the virtual representation and wherein the results of the comparison include the degree of overlap.

In Example 51, the subject matter of Example 50 optionally includes in response to determining the degree of overlap is above a threshold, projecting, using the augmented reality display, the virtual representation in a green color, and in response to determining the degree of overlap is below the threshold, projecting, using the augmented reality display, the virtual representation in a red color.

In Example 52, the subject matter of any one or more of Examples 49-51 optionally include wherein the aspect of the preoperative plan includes a virtual representation of a trial and wherein the surgical component is the trial.

In Example 53, the subject matter of Example 52 optionally includes presenting, using the augmented reality display, a virtual representation of an extension or flexion gap thickness.

In Example 54, the subject matter of any one or more of Examples 52-53 optionally include wherein the trial includes laser markings for tracking an orientation of the trial.

In Example 55, the subject matter of any one or more of Examples 52-54 optionally include projecting, using the augmented reality display, a proposed bearing thickness option based on known resections and locations of the trial.

In Example 56, the subject matter of any one or more of Examples 49-55 optionally include wherein the aspect includes a virtual guide.

In Example 57, the subject matter of Example 56 optionally includes wherein the virtual guide includes a funneling cone for pin placement.

In Example 58, the subject matter of Example 57 optionally includes wherein the funneling cone narrows down to a pin point on a femur.

In Example 59, the subject matter of any one or more of Examples 49-58 optionally include detecting a gesture from a surgeon to change the preoperative plan.

In Example 60, the subject matter of any one or more of Examples 49-59 optionally include in response to the results of the comparison being output by the processor, presenting, using the augmented reality display, a visual indication of the results.

In Example 61, the subject matter of any one or more of Examples 49-60 optionally include in response to the results of the comparison being output, playing an audible alert or indication of the results.

In Example 62, the subject matter of any one or more of Examples 49-61 optionally include in response to the results of the comparison being output, causing a vibration to indicate the results.

Example 63 is at least one machine readable medium including instructions for using an augmented reality device during a surgical procedure, which when executed by a machine, cause the machine to: project, using an augmented reality display of the augmented reality device, a virtual representation of an aspect of a preoperative plan at a planned location within a surgical field while permitting the surgical field to be viewed through the augmented reality display; capture, using a camera, an image of a surgical component within the surgical field; compare a location of the surgical component within the surgical field from the captured image to the planned location within the preoperative plan; and output results of the comparison.

In Example 64, the subject matter of Example 63 optionally includes wherein the aspect of the preoperative plan includes a virtual representation of an implant and wherein the surgical component is the implant, and wherein the instructions to compare the location of the surgical component to the planned location include instructions to determine a degree of overlap between the surgical component and the virtual representation and wherein the results of the comparison include the degree of overlap.

In Example 65, the subject matter of Example 64 optionally includes in response to determining the degree of overlap is above a threshold, instructions to project, using the augmented reality display, the virtual representation in a green color, and in response to determining the degree of overlap is below the threshold, instructions to project, using the augmented reality display, the virtual representation in a red color.

In Example 66, the subject matter of any one or more of Examples 63-65 optionally include wherein the aspect of the preoperative plan includes a virtual representation of a trial and wherein the surgical component is the trial.

In Example 67, the subject matter of Example 66 optionally includes instructions to present, using the augmented reality display, a virtual representation of an extension or flexion gap thickness.

In Example 68, the subject matter of any one or more of Examples 66-67 optionally include wherein the trial includes laser markings for tracking an orientation of the trial.

In Example 69, the subject matter of any one or more of Examples 66-68 optionally include instructions to project, using the augmented reality display, a proposed bearing thickness option based on known resections and locations of the trial.

In Example 70, the subject matter of any one or more of Examples 63-69 optionally include wherein the aspect includes a virtual guide.

In Example 71, the subject matter of Example 70 optionally includes wherein the virtual guide includes a funneling cone for pin placement.

In Example 72, the subject matter of Example 71 optionally includes wherein the funneling cone narrows down to a pin point on a femur.

In Example 73, the subject matter of any one or more of Examples 63-72 optionally include instructions to detect a gesture from a surgeon to change the preoperative plan.

In Example 74, the subject matter of any one or more of Examples 63-73 optionally include in response to the results of the comparison being output by the processor, instructions to present, using the augmented reality display, a visual indication of the results.

In Example 75, the subject matter of any one or more of Examples 63-74 optionally include in response to the results of the comparison being output, instructions to play an audible alert or indication of the results.

In Example 76, the subject matter of any one or more of Examples 63-75 optionally include in response to the results of the comparison being output, instructions to cause a vibration to indicate the results.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. An augmented reality device for use during a surgical procedure comprising:
   an augmented reality display to project a virtual representation of an aspect of a preoperative plan at a planned location within a surgical field while permitting the surgical field to be viewed through the augmented reality display;
   a sensor to capture location and orientation information of a surgical component within the surgical field; and
   a processor to:
   compare the location of the surgical component within the surgical field to the planned location within the preoperative plan, the comparing including determining a degree of overlap between the surgical component and the virtual representation;
   determine the degree of overlap transgresses an overlap threshold; and
   in response to determining the degree of overlap transgresses the overlap threshold, cause the augmented reality display to project a changed virtual representation.

2. The augmented reality device of claim 1, wherein the aspect of the preoperative plan includes a virtual representation of an implant and wherein the surgical component is the implant.

3. The augmented reality device of claim 1, wherein, in response to determining the degree of overlap transgresses the overlap threshold, the augmented reality display is further to project the virtual representation in a first color, and in response to determining the degree of overlap does not transgress the overlap threshold, the augmented reality display is further to project the virtual representation in a second color.

4. The augmented reality device of claim 1, wherein the aspect of the preoperative plan includes a virtual representation of a trial and wherein the surgical component is the trial.

5. The augmented reality device of claim 4, wherein the augmented reality display is further to present a virtual representation of an extension-flexion gap thickness.

6. The augmented reality device of claim 4, wherein the trial includes laser markings for tracking an orientation of the trial.

7. The augmented reality device of claim 4, wherein the augmented reality display is further to project a proposed bearing thickness option based on known resections and locations of the trial.

8. The augmented reality device of claim 1, wherein the sensor is further to detect a gesture from a surgeon to change the preoperative plan.

9. The augmented reality device of claim 1, wherein the preoperative plan includes a range of motion, the virtual representation of the aspect of the preoperative plan includes a virtual range of motion visual effect, and the surgical component includes a patient limb to be moved through the range of motion.

10. The augmented reality device of claim 1, wherein the sensor includes a camera to capture an image of a surgical component within the surgical field.

11. A method for using an augmented reality device during a surgical procedure comprising:
   projecting, using an augmented reality display of the augmented reality device, a virtual representation of an aspect of a preoperative plan at a planned location within a surgical field while permitting the surgical field to be viewed through the augmented reality display;
   capturing a location and orientation of a surgical component within the surgical field using a tracking device;
   comparing, using a processor, the location of the surgical component within the surgical field to the planned location within the preoperative plan, the comparing including determining a degree of overlap between the surgical component and the virtual representation;
   determining the degree of overlap transgresses an overlap threshold; and
   in response to determining the degree of overlap transgresses an overlap threshold, causing the augmented reality display to project a changed virtual representation.

12. The method of claim 11, further comprising, in response to determining the degree of overlap transgresses the overlap threshold, projecting, using the augmented reality display, the virtual representation in a first color, and in response to determining the degree of overlap does not transgress the overlap threshold, projecting, using the augmented reality display, the virtual representation in a second color.

13. The method of claim 11, further comprising detecting a gesture from a surgeon to change the preoperative plan.

14. At least one machine readable medium including instructions for using an augmented reality device during a surgical procedure, which when executed by a machine, cause the machine to:
   project, using an augmented reality display of the augmented reality device, a virtual representation of an aspect of a preoperative plan at a planned location within a surgical field while permitting the surgical field to be viewed through the augmented reality display;
   capture, using a camera, an image of a surgical component within the surgical field;
   compare a location of the surgical component within the surgical field from the captured image to the planned location within the preoperative plan, the comparing including determining a degree of overlap between the surgical component and the virtual representation;
   determine the degree of overlap transgresses an overlap threshold; and
   in response to determining the degree of overlap transgresses an overlap threshold, cause the augmented reality display to project a changed virtual representation.

15. The at least one machine readable medium of claim 14, further comprising, in response to determining the degree of overlap transgresses the overlap threshold, instructions to project, using the augmented reality display, the virtual representation in a first color, and in response to determining the degree of overlap does not transgress the overlap threshold, instructions to project, using the augmented reality display, the virtual representation in a second color.

16. The at least one machine readable medium of claim 14, further comprising instructions to detect a gesture from a surgeon to change the preoperative plan.

17. The at least one machine readable medium of claim 14, further comprising, in response to determining the degree of overlap transgresses an overlap threshold, instructions to present, using the augmented reality display, a visual indication of the results.

* * * * *